United States Patent
Madsen et al.

[11] Patent Number: 6,086,533
[45] Date of Patent: Jul. 11, 2000

[54] NON-INVASIVE IN VIVO PRESSURE MEASUREMENT

[75] Inventors: Joseph R. Madsen, Newton; George A. Taylor, Wellesley, both of Mass.

[73] Assignee: Children's Medical Center Corporation, Boston, Mass.

[21] Appl. No.: 09/097,067

[22] Filed: Jun. 12, 1998

[51] Int. Cl.[7] .................................................. A61B 8/00
[52] U.S. Cl. .......................................... 600/438; 600/561
[58] Field of Search .................................. 600/437, 438, 600/480, 489–490, 494, 495, 561

[56] References Cited

U.S. PATENT DOCUMENTS

| | | | |
|---|---|---|---|
| 4,033,178 | 7/1977 | Holt et al. | 73/71.5 |
| 4,127,114 | 11/1978 | Bretscher | 600/480 |
| 4,203,451 | 5/1980 | Panico | 600/485 |
| 4,237,901 | 12/1980 | Taenzer | 128/660 |
| 4,566,462 | 1/1986 | Janssen | 600/490 |
| 4,995,401 | 2/1991 | Bunegin et al. | 600/561 |
| 5,452,722 | 9/1995 | Langton | 128/660.06 |
| 5,454,372 | 10/1995 | Banjanin et al. | 128/661.08 |
| 5,479,928 | 1/1996 | Cathignol et al. | 128/662.06 |
| 5,487,389 | 1/1996 | Banjanin et al. | 128/661.09 |
| 5,503,156 | 4/1996 | Millar | 128/672 |
| 5,575,289 | 11/1996 | Skidmore | 128/661.08 |
| 5,615,681 | 4/1997 | Ohtomo | 128/661.03 |
| 5,628,322 | 5/1997 | Mine | 128/661.08 |
| 5,640,960 | 6/1997 | Jones et al. | 128/661.07 |
| 5,701,898 | 12/1997 | Adam et al. | 128/661.09 |
| 5,738,097 | 4/1998 | Beach et al. | 128/661.09 |
| 5,951,477 | 9/1999 | Ragauskas et al. | 600/438 |

FOREIGN PATENT DOCUMENTS

| | | | |
|---|---|---|---|
| 0299827 | 1/1989 | European Pat. Off. | A61B 5/02 |
| 2602663 | 2/1988 | France | A61B 5/02 |
| WO 85/00278 | 1/1985 | WIPO | A61B 5/02 |
| WO 95/00074 | 1/1995 | WIPO | A61B 8/04 |

*Primary Examiner*—Francis J. Jaworski
*Attorney, Agent, or Firm*—Thomas J. Engellenner; Nutter, McClennen & Fish, LLP

[57] ABSTRACT

Apparatus and methods are disclosed for non-invasive measurement of blood velocity in otherwise inaccessible body regions, and for correlating such measurements with externally applied pressure to detect and/or assess diseases or physiological abnormalities. The blood velocity measurements can be based on the Doppler shift that occurs when an ultrasonic wave is scattered by moving particles within the blood. Since blood vessels have elastic walls, the geometry of the walls, and therefore the flow dynamics, will change in response to elevated in vivo pressure. The change in resistance to blood flow resulting from these pressure induced changes to the blood vessel wall geometry can provide a measure of intracranial pressure, ophthalmic pressure or various other body conditions that affect blood perfusion. Since the blood vessel wall geometry changes rapidly in response to such changes in pressure, the invention can be used to detect hydrocephalus, retinopathy, papilledema and other physiological abnormalities manifested by pressure changes.

11 Claims, 1 Drawing Sheet

NON-INVASIVE IN VIVO PRESSURE MEASUREMENT

BACKGROUND OF THE INVENTION

The technical field of this invention is medical sonography and, in particular, methods and devices for employing ultrasonic measurements of blood flow to detect and assess diseases or physiological abnormalities.

Inside the brain is a ventricular system which contains and conducts cerebrospinal fluid. This cerebrospinal fluid flows through several ventricles within the brain before being absorbed back into the blood. When drainage is blocked, the buildup of fluid results in a pressure which swells the ventricles and increases the pressure throughout the brain. This causes a condition referred to as "hydrocephalus."

Although the intracranial pressure increase associated with hydrocephalus can be relieved surgically by providing a shunt from the ventricle to the peritoneum, this too can frequently result in complications. Accordingly, it is desirable to provide a method and apparatus for reliably measuring the intracranial pressure.

Intracranial pressure can be measured directly by surgically inserting a pressure transducer inside the cranium. However, the inconvenience of surgery and the necessity of penetrating the skull make this method undesirable.

Indirect evidence of intracranial pressure can be obtained by observing the effect of elevated pressure on the structures inside the cranium. For example, one can ultrasonically measure the size of the ventricle and determine whether it is unusually large or whether it has increased in size.

However, a hemorrhage, either inside the ventricle or in adjacent parenchymal tissue, can obscure the ventricle and make inferences about pressure from observation of its size difficult. Since hydrocephalus is a frequent complication of intracranial hemorrhage in premature infants, this difficulty is frequently encountered in practice.

An additional disadvantage of the above method is that detectable enlargement of the ventricle requires that the hydrocephalus be chronic. Thus, by the time the elevated intracranial pressure is detected, some damage may have already occurred to the intracranial structures.

The difficulty in obtaining the intracranial pressure, as described above, is a manifestation of the more general difficulty of measuring pressure at inaccessible locations within the human body. The process of measuring pressure in, for example, a blood vessel, involves the application of a mechanical pressure to the vessel itself. Typically, an inflatable cuff is placed around an arm and inflated until it cuts off the blood flow. The cuff pressure required to stop the blood flow provides a measure of the pressure driving that flow.

The foregoing method of applying a mechanical pressure to a blood vessel is not well suited for the measurement of pressure in specific blood vessels. For example, in a diabetic patient afflicted with papilledema, it is often desirable to measure the blood pressure in the capillaries leading to the eye. The use of the conventional inflatable cuff to measure blood pressure within the capillaries leading to the retina is made difficult by the lack of a suitable site at which to apply the inflatable cuff.

In some cases, even when a suitable pressure application site is available, the process of inflating the cuff until it cuts off blood flow may be highly intrusive. For example, measurement of local blood pressure using a cuff in connection with the treatment of impotence is hardly a practical option.

An additional disadvantage of the traditional method of measuring blood pressure is that it is unable to detect the rate of change of blood flow as a function of applied pressure. Using the traditional method, one can readily establish the pressure at which blood flow through a vessel ceases. However, one cannot determine, for example, whether the blood velocity began to decrease precipitously at a particular applied pressure or whether it decreased gradually throughout the process of applying an external pressure.

It is an object of this invention to provide a method and apparatus for measuring pressure at specific sites in the body in a non-invasive manner.

It is a further object of the invention to provide a method and apparatus for determining the effect of an applied pressure or blood flow across a broad range of applied pressures.

SUMMARY OF THE INVENTION

Apparatus and methods are disclosed for non-invasive measurement of blood velocity in otherwise inaccessible regions, and for correlating such measurements with externally applied pressure to detect and/or assess diseases or physiological abnormalities. The blood velocity measurements can be based on the Doppler shift that occurs when an ultrasonic wave is scattered by moving particles within the blood. Since blood vessels have elastic walls, the geometry of the walls, and therefore the flow dynamics, will change in response to elevated in vivo pressure. The change in resistance to blood flow resulting from these pressure induced changes to the wall geometry can provide a measure of intracranial pressure, ophthalmic pressure or various other body conditions that affect blood perfusion. Since wall geometry changes rapidly in response to such changes in pressure, the invention can be used to detect hydrocephalus, glaucoma, retinopathy, papilledema and other physiological abnormalities manifested by pressure changes.

An apparatus, according to the invention, which uses the change in blood flow to measure the pressure driving that flow includes a pressure applicator containing an acoustically transmitting medium through which ultrasonic waves can propagate between the blood vessel or other intracorporeal fluid and an ultrasonic transducer. In one preferred embodiment, the pressure applicator is a bladder filled with an acoustically transparent liquid, such as water, and having a deformable side wall which contacts the skin along a contact area.

The pressure applicator is preferably coupled to a pressure sensor, which measures the pressure applied by the pressure applicator to the surface of the patient, and can be integrated with, or adapted to couple to, an ultrasonic transducer which transmits and receives ultrasonic waves.

Both the pressure applicator and the ultrasonic transducer are in communication with a data processor which uses the received pressure data and ultrasonic signal in the conventional manner to derive the in vivo pressure of the intracorporeal fluid.

Thus, the invention permits an inferred estimation of in vivo pressure based on the compliance of the target tissue and effect of an externally applied pressure on the hemodynamics in the tissue.

BRIEF DESCRIPTION OF THE DRAWINGS

These and other features, aspects and advantages of the invention will be better understood with reference to the accompanying drawings in which.

DETAILED DESCRIPTION

Figure 1:
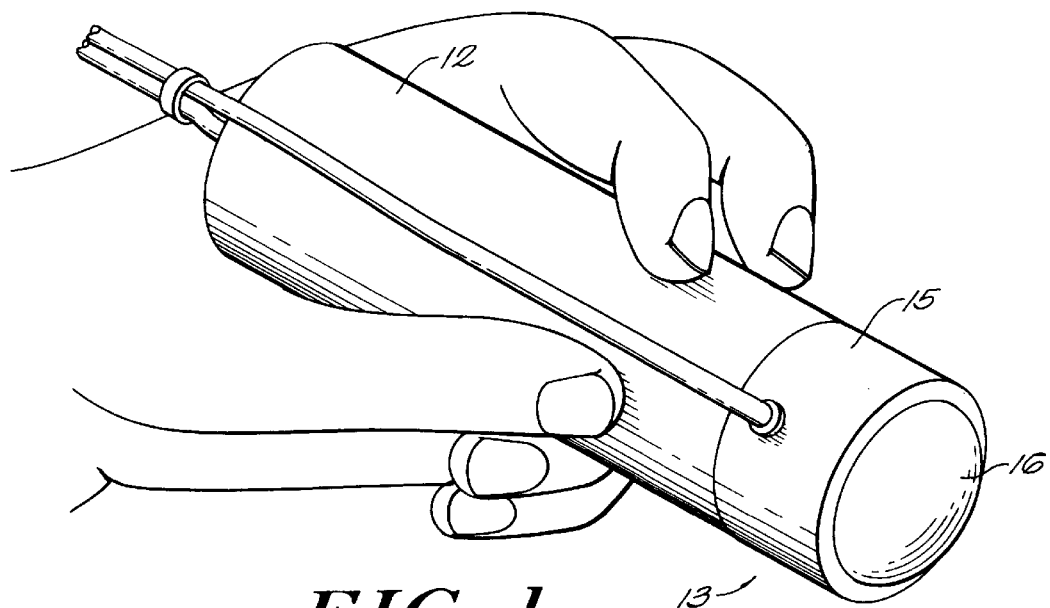
FIG. 1 is a schematic perspective view of an ultrasound probe and pressure measurement apparatus according to the invention.

In FIG. 1, a non-invasive pressure measurement apparatus 10 according to the invention includes a hand-held ultrasound probe 12. The geometry of the probe 12 is not critical but can be chosen for ease of manipulation. Various commercially available ultrasound systems can be used to provide an ultrasound probe 12 and to transmit and receive ultrasonic waves, as well as to provide Doppler shift data. For an exemplary discussion of such ultrasound systems, see U.S. Pat. No. 5,640,960 which is incorporated herein by reference.

A pressure applicator 13, which includes a housing 15 and a bladder 16 filled with an acoustically transparent medium 18, is mounted to one end of the ultrasound probe 12. Preferably, the bladder is a flexible structure which deforms in response to the pressure exerted by it bladder on a surface. The acoustically transparent medium can be water, a saline solution, or any other acoustically transparent liquid or gel.

Figure 2:
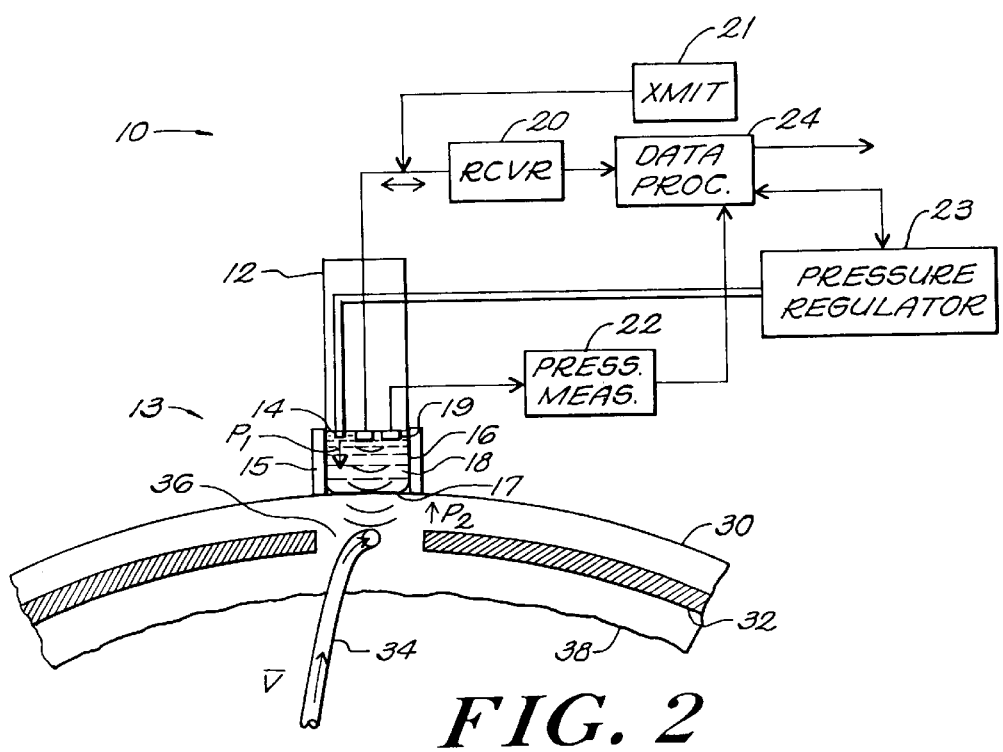
FIG. 2 shows an apparatus according to the invention resting on the skin covering a fontanelle in a neonatal cranium.

As shown in more detail in FIG. 2, the pressure applicator 13 preferably includes a pressure transducer 19 which is responsive to the pressure exerted by the bladder on a surface. The pressure transducer 19 is coupled to a pressure measurement circuit 22, the output of which becomes an input to a data processor 24. The pressure applicator 13 can be incorporated into a special purpose ultrasound probe or designed as an adapter which is coupled to a conventional probe.

An ultrasonic transducer 14 incorporated into the probe 12 converts electronic signals into ultrasonic waves that are transmitted into the medium 18 and, conversely, converts ultrasonic waves returning back from the medium 18 into electrical signals. The ultrasonic transducer 14 is electrically coupled to both a waveform generator 21 and a waveform detector 20. Alternatively, the functions of the transducer can be performed by one or more separate transmitters or receivers. A housing 15 can surround the bladder 16 to constrain deformation of the bladder when pressure is applied.

In operation, the clinician positions the pressure applicator 13 on the skin over the region in which the blood pressure is to be measured. In FIG. 1, the pressure applicator 13 is shown on the skin 30 covering a fontanelle 36 in a neonatal cranium 32. The clinician applies an external pressure $P_1$ by pressing a contact surface 17 of the pressure applicator 13 against the skin 30. The pressure thus generated by the operator is transmitted, by way of the fluid within the bladder 16, to a pressure transducer 19 which generates an electrical signal representative of the applied external pressure for processing by the pressure measurement circuit 22. Accordingly, a pressure regulation 23 can be used to regulate the pressure applied by the bladder's contact surface or to implement an automated or pre-defined protocol of applied pressure. Such a protocol can be initiated or controlled by data processor 24.

The above procedure can be performed at sites other than the illustrated fontanelle. For example, the apparatus 10 can be placed against a closed eyelid. In such a case, the fluid in the bladder 16 can be acoustically coupled, through the vitreous humor of the eye, to the capillaries feeding the retina for measurement of blood pressure in those capillaries.

The waveform generator 21 transmits an electrical signal to the transducer 14 which then converts it into an ultrasonic wave. The ultrasonic wave propagates through the acoustically transparent medium 18 in the bladder 16 and crosses the skin/bladder interface. As shown in the illustrative example of FIG. 1, the fontanelle 36, over which the bladder rests, provides an aperture through which ultrasonic waves crossing the bladder/skin interface can penetrate the cranium 32 and illuminate a blood vessel 34. Ultrasonic waves crossing the bladder/skin interface propagate through the skin 30 and illuminate blood vessels 34 within the brain 38.

The interaction of the incident ultrasonic radiation with the blood flow within the blood vessel 34 results in a reflected ultrasonic wave having a frequency shifted by an amount representative of the velocity of the blood within the blood vessel. This Doppler shifted ultrasonic wave exits the cranium through the fontanelle 36, crosses the interface between the skin and the bladder, and propagates through the acoustically transparent medium 18 within the bladder 16. The reflected wave impinges on the ultrasonic transducer 14 and thereby generates an electrical signal representative of the reflected wave. This electrical signal is then transmitted to waveform detector 20.

The pressure $P_1$ applied by the operator against the skin 30 affects the blood velocity in the blood vessel 34. Since the reflected ultrasonic wave provides a measure of the blood velocity, this wave is likewise affected by the applied external pressure $P_1$. The measured values of the reflected ultrasonic wave are transmitted to a data processor 24 together with the measured values of external pressure $P_1$. The data processor 24 then uses these two quantities to determine the internal pressure $P_2$ within the cranium 32.

It will thus be seen that the invention efficiently attains the objects set forth above. Since certain changes may be made in the above construction without departing from the scope of the invention, it is intended that all matter contained in the above description or shown in the accompanying drawings be interpreted as illustrative and not limiting. In particular, the illustration of measurements at the fontanelle should be understood to be merely exemplary. The apparatus can be applied to the ophthalmic region to detect retinopathies or applied to the skin to detect venous occlusions. Moreover, it may be preferable, in some applications, to take measurements of the ophthalmic region to detect and/or assess intracranial abnormalities (particularly, in adults whose fontanelle regions have fused).

It is also to be understood that the following claims are intended to cover all generic and specific features of the invention described herein. When describing the invention, what is claimed as new and secured by Letters Patent is:

What is claimed is:

1. An apparatus for ultrasonically evaluating an in vivo pressure, the apparatus comprising:

an ultrasonic transducer for transmitting a first ultrasonic wave to an in vivo target region and detecting a second ultrasonic wave reflected from the in vivo target region, the second ultrasonic wave having a frequency shifted by an amount corresponding to a velocity of blood within a blood vessel in the in vivo target region;

a pressure applicator acoustically coupled to the ultrasonic transducer for applying an external pressure to the target region to alter the blood velocity in the blood vessel, the pressure applicator being filled with an acoustically transmissive medium for propagation of the first and second ultrasonic waves between the transducer and the target region;

a pressure sensor coupled to the pressure applicator for measuring the external pressure applied by the pressure applicator at the target region; and a data processor in communication with the pressure sensor and the ultrasonic transducer for directly evaluating an in vivo pressure from the external pressure and the blood velocity in the blood vessel within the in vivo target region as determined from the first and second ultrasonic waves based upon a predetermined correspondence between the external pressure and changes in the blood velocity in the blood vessel within the target region due to the external pressure.

2. The apparatus according to claim 1 wherein the pressure applicator comprises a bladder filled with an acoustically transmissive medium.

3. The apparatus of claim 1 wherein the acoustically transmissive medium comprises a liquid.

4. The apparatus of claim 3 wherein the liquid is water.

5. The apparatus of claim 1 wherein the pressure applicator is adapted for placement against a fontanelle on the neonatal cranium.

6. A method for ultrasonically evaluating an in vivo pressure, the method comprising the steps of:

applying a pressure applicator filled with an acoustically transmissive medium to the target region, thereby developing an external pressure in the target region;

transmitting a first ultrasonic wave into the target region;

detecting a second ultrasonic wave, the second ultrasonic wave generated by an interaction between the first ultrasonic wave and the target region;

measuring the applied external pressure, thereby generating an external pressure measurement;

calculating the in vivo pressure in the target region based on the first and second ultrasonic waves including a shift in frequency of the second ultrasonic wave corresponding to a velocity of blood in a blood vessel in the target region and on the external pressure measurement, wherein there is a predetermined correspondence between the external pressure and changes in the blood velocity due to the external pressure.

7. The method of claim 6 wherein the step of applying an external pressure to the target region comprises the step of placing a bladder against the target region, the bladder being filled with an acoustically transmissive medium.

8. The method of claim 7 wherein the step of measuring the applied external pressure comprises the step of providing a transducer coupled to the bladder.

9. The method according to claim 8 wherein the acoustically transmissive medium is a liquid.

10. The method according to claim 9 wherein the liquid is water.

11. The method according to claim 6 further comprising the step of selecting the target region to be a neonatal cranium and the step of measuring the applied external pressure includes the step of placing the pressure applicator against a fontanelle on the cranium.

* * * * *